(12) United States Patent
Yamauchi (10) Patent No.: US 7,584,647 B2
(45) Date of Patent: Sep. 8, 2009

(54) STRUCTURE OF GAS SENSOR DESIGNED TO ENSURE STABILITY OF WATERPROOFING AND AIR VENTILATION

(75) Inventor: Masanobu Yamauchi, Kariya (JP)

(73) Assignee: Denso Corporation, Kariya (JP)

( * ) Notice: Subject to any disclaimer, the term of this patent is extended or adjusted under 35 U.S.C. 154(b) by 218 days.

(21) Appl. No.: 11/727,230

(22) Filed: Mar. 26, 2007

(65) Prior Publication Data

US 2007/0227232 A1   Oct. 4, 2007

(30) Foreign Application Priority Data

Mar. 31, 2006   (JP) .............................. 2006-099192

(51) Int. Cl.
*G01N 7/00* (2006.01)
*G01N 27/02* (2006.01)
(52) U.S. Cl. ..................................... 73/31.05; 204/424
(58) Field of Classification Search ................ 73/31.05; 204/424
See application file for complete search history.

(56) References Cited

U.S. PATENT DOCUMENTS

2003/0136675 A1 * 7/2003 Ishikawa ................. 204/424

2004/0129566 A1 * 7/2004 Nakagawa ................. 204/424

FOREIGN PATENT DOCUMENTS

JP          2001-235445          8/2001

* cited by examiner

*Primary Examiner*—Lisa M Caputo
*Assistant Examiner*—Punam Patel
(74) *Attorney, Agent, or Firm*—Nixon & Vanderhye, PC (57) ABSTRACT

A gas sensor designed to ensure waterproofing and air ventilation is provided which includes a rubber bush fitted in an end of an air cover joined to a housing. The rubber bush has formed in a base portion thereof lead-pass holes and in a top portion thereof an air flow path through which air is introduced into an air chamber in the gas sensor. The air cover is crimped circumferentially to provide an elastic nip only to the base portion of the rubber bush, thereby ensuring tight fits of the leads in the lead-pass holes without deforming the air flow path undesirably. An ventilation filter is fit on a neck of the rubber bush between the base portion and the top portion in communication with the air flow path, thus ensuring the stability of entrance of the air into the air flow path through the ventilation filter.

7 Claims, 14 Drawing Sheets

STRUCTURE OF GAS SENSOR DESIGNED TO ENSURE STABILITY OF WATERPROOFING AND AIR VENTILATION

CROSS REFERENCE TO RELATED DOCUMENT

The present application claims the benefit of Japanese Patent Application No. 2006-99192 filed on Mar. 31, 2006, the disclosures of which are incorporated herein by reference.

BACKGROUND OF THE INVENTION

1. Technical Field of the Invention

The present invention relates generally to a gas sensor which may be employed in measuring the concentration of a selected component of exhaust gasses emitted from automotive engines for use in air-fuel ratio control, and more particularly to an improved structure of such a gas sensor which is equipped with a built-in air ventilation filter and designed to ensure the stability of waterproofing and ventilation.

2. Background Art

Figure 18:
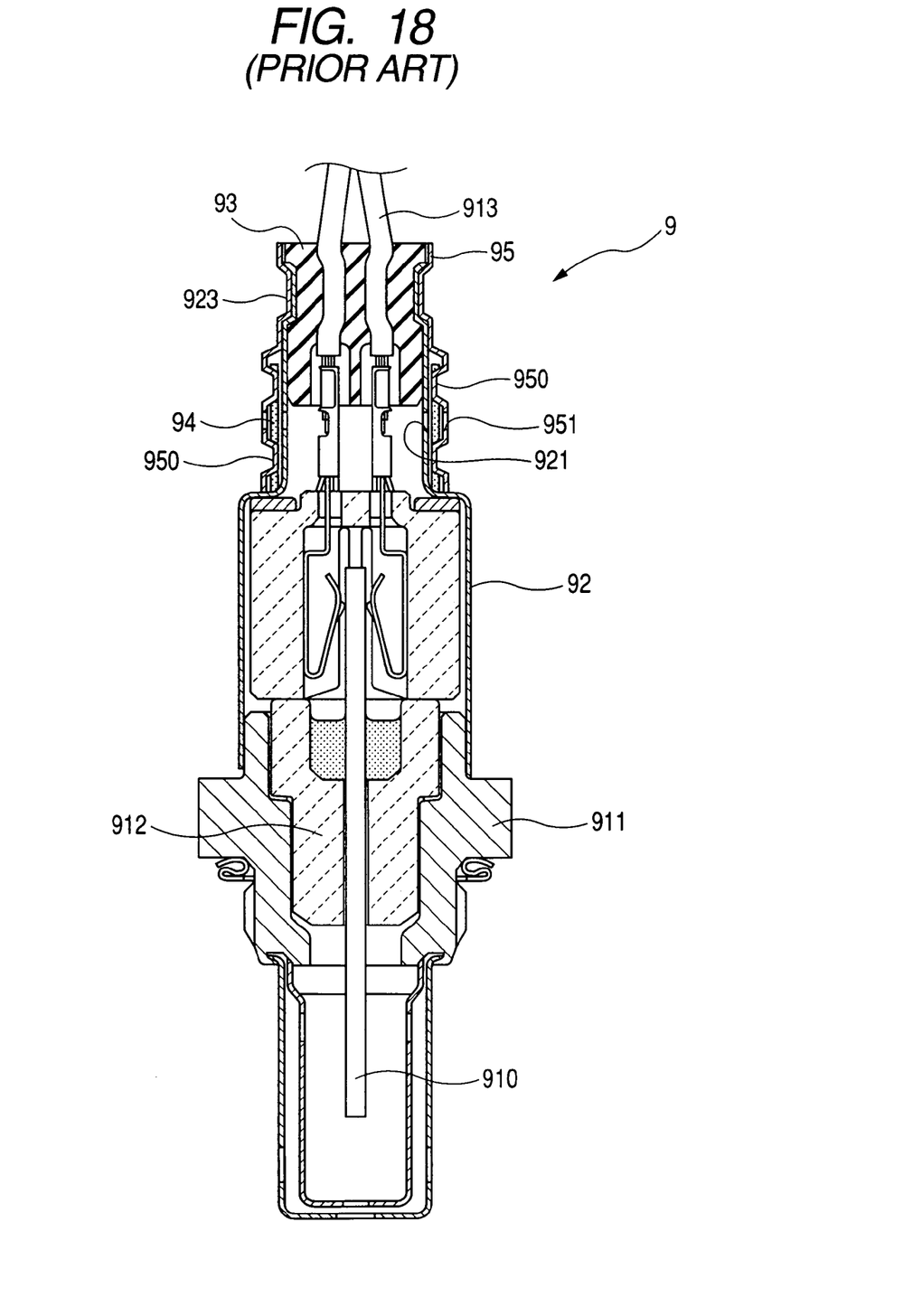
FIG. 18 is a longitudinal sectional view which shows an internal structure of a conventional gas sensor.

There are known gas sensors to be installed in an exhaust pipe of an internal combustion engine for automotive vehicles to measure the concentration of oxygen ($O_2$) contained in exhaust emissions. FIG. 18 shows such a type of a gas sensor 9.

The gas sensor 9 consists essentially of a sensor element 910 to measure the concentration of a gas (will also be referred to below as a measurement gas), a housing 911 in which the sensor element 910 is retained through a porcelain insulator 912, and an air cover 92 joined to a base end (i.e., an upper end, as viewed in the drawing) of the housing 911.

A rubber bush 93 is fitted in the base end of the air cover 92 to form a hermetic seal therein. The rubber bush 93 also retains therein leads 913 connecting electrically with the sensor element 910.

An outer cover 95 is fitted around a base end portion of the air cover 92. The joint between the outer cover 95 and the air cover 92 is achieved by pressing or crimping them radially inwardly to form an annular crimped portion 923.

A water-proof ventilation filter 94 is nipped firmly between the air cover 92 and the outer cover 95 by two annular crimped portions 950 which are away from each other in an axial direction of the gas sensor 9. The outer cover 95 has formed therein air intake openings 951 which face air intake holes 921 through the ventilation filter 94. Fresh air is introduced as a reference gas from the air intake openings 951 inside the gas sensor 9 through the ventilation filter 94 and the air intake holes 921.

However, the arrangement of the ventilation filter 94 between the air cover 92 and the outer cover 95 undesirably facilitates the transmission of thermal energy from the air cover 92 and/or the outer cover 95 to the ventilation filter 94. A long-term exposure of the gas sensor 9 to exhaust gas from the internal combustion engine will, therefore, result in thermal deterioration of the ventilation filter 94, which leads to reduction in waterproofing property of the ventilation filter 94 at the crimped portions 950, so that water may enter the gas sensor 9 at the air intake holes 921.

Figure 19:
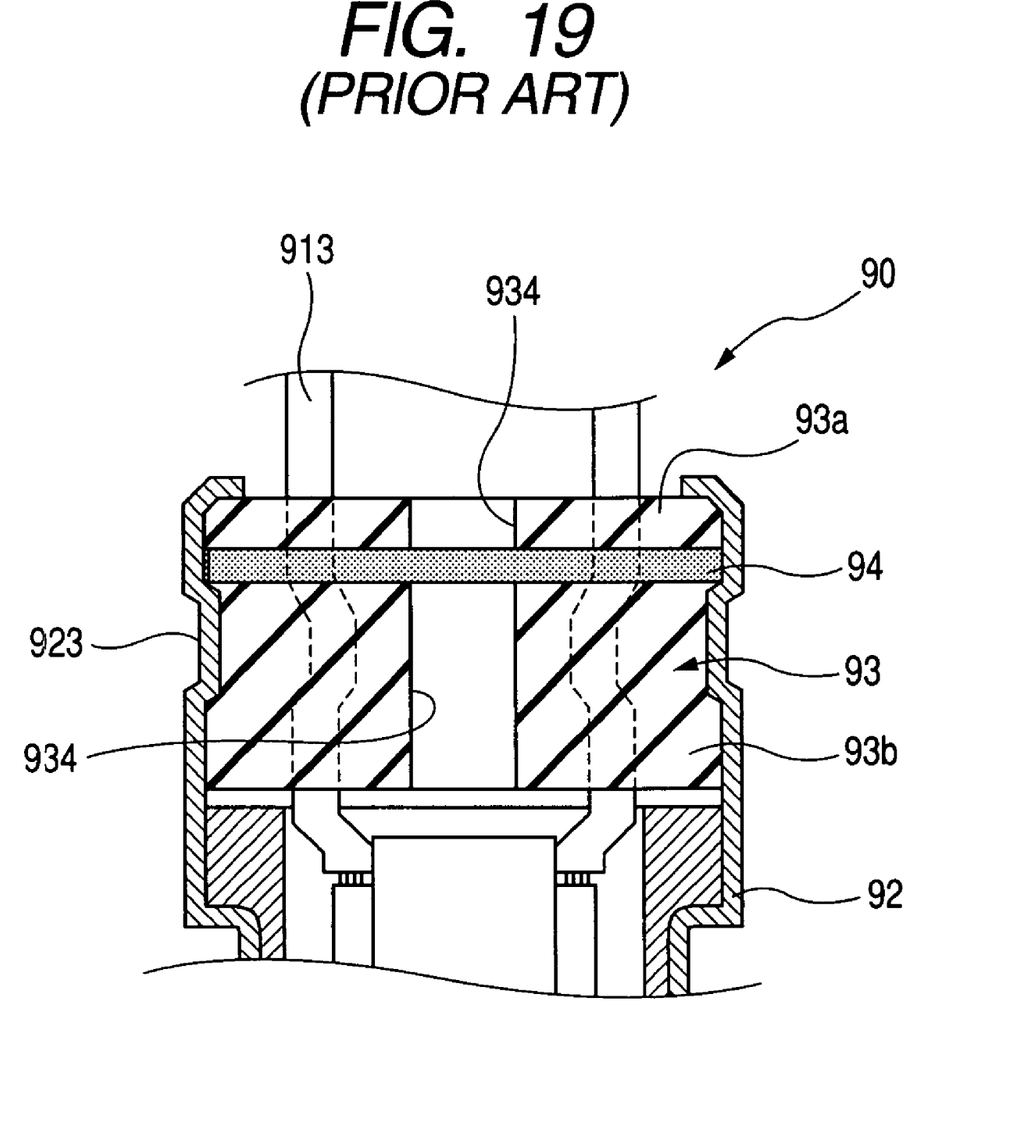
FIG. 19 is a partially enlarged longitudinal sectional view which shows a base end portion of another type of a conventional gas sensor.

Japanese Patent First Publication No. 2001-235445 discloses a gas sensor 90, as illustrated in FIG. 19, which is equipped with a rubber bush 93 made up of two parts: an upper rubber block 93a and a lower rubber block 93b which have center air inlet holes 934 and hold a ventilation filter 94 firmly therebetween.

The gas sensor 90, however, has the following drawback.

The rubber bush 93 is pressed inwardly at all times by crimping the circumference of the air cover 92 to form a crimped portion 923. This may cause the air inlet holes 934 to deformed elastically, resulting in a lack in amount of air introduced into the gas sensor 90 through the center intake holes 934.

SUMMARY OF THE INVENTION

It is therefore a principal object of the invention to avoid the disadvantages of the prior art.

It is another object of the invention to provide an improved structure of a gas sensor designed to ensure the water resistance and ventilation for long-term use.

According to one aspect of the invention, there is provided a gas sensor which may be employed in measuring the concentration of a component of exhaust gasses emitted from automotive engines. The gas sensor has a length with a top end and a base end opposite the top end and comprises: (a) a sensor element sensitive to a gas to produce a signal as a function of concentration of the gas; (b) a housing in which the sensor element is retained, the housing having a top end and a base end opposite the top end; (c) an elastic block having holes through which leads pass to connect electrically with the sensor element, the elastic block being made up of a top portion closer to the top end of the gas sensor, a base portion closer to the base end of the gas sensor, and a neck formed between the top portion and the base portion, the base portion having a first shoulder surface, the top portion having a second shoulder surface facing the first shoulder surface in a lengthwise direction of the gas sensor; (d) an air flow path extending within the top portion of the elastic block, the air flow path having an air inlet and an air outlet, the air inlet opening on an outer surface of the neck of the elastic block, the air outlet opening on a surface of the top portion of the elastic block exposed to an air chamber leading to the sensor element; (e) an annular ventilation filter fitted on the neck of the elastic block in communication with the air inlet of the air flow path to permit air to enter the air flow path from outside the elastic block through the ventilation filter, the ventilation being nipped between the first and second shoulder surfaces of the elastic block; (f) an air cover joined to the housing to extend away from the base end of the gas sensor to define therein the air chamber to which the air outlet of the air flow path is exposed, the air cover being crimped to provide a lateral elastic nip to the base portion of the elastic block in a direction perpendicular to the lengthwise direction of the gas sensor and also crimped to provide a longitudinal elastic nip to the elastic block in the lengthwise direction of the gas sensor; and (g) an air inlet hole formed in the air cover through which the air is admitted to the ventilation filter.

The ventilation filter is fit on the neck of the elastic block while being compressed between the first and second shoulder surfaces. Therefore, when the ventilation filter is thermally deteriorated and shrunk, the elastic block elastically expands to compensate for the amount of shrinkage of the ventilation filter, thereby keeping the fitting of the ventilation filter to the elastic block to ensure a liquid-tight seal between the ventilation filter and the elastic block.

The air cover is, as described above, crimped to provide the lateral elastic nip only to the base portion of the elastic block in the direction perpendicular to the lengthwise direction of the gas sensor, thus ensuring a tight fit of each of the leads within one of the holes in the elastic block without sacrificing a desired volume of air flowing through the air flow path. Such a tight fit minimizes a gap between each of the leads and one of the holes and also results in an increased resistance of the holes to deformation thereof, thereby ensuring a liquid-tight seal in the base end of the gas sensor.

In the preferred mode of the invention, the top portion and the base portion of the elastic block are greater in diameter than the neck. The ventilation filter is fitted around a periphery of the neck.

The top portion and the base portion of the elastic block may be made of discrete parts, the top portion and the base portion being arranged to provide a longitudinal elastic nip to the ventilation filter in the lengthwise direction of the gas sensor. The base portion has a small-diameter portion. The top portion may be made of a ring member with an opening fit on the small-diameter portion of the base portion to define the neck of the elastic block.

The air cover may be made of an assembly of a protective cover and a support cover. The protective cover has a base end and a top end opposite the base end and surrounds the elastic block. The support cover has a base end and a top end opposite the base end. The protective cover is fitted on the support cover to elastically nip the elastic block between the base ends of the protective cover and the support cover in the lengthwise direction of the gas sensor.

The protective cover is fitted on the support cover through crimped joints which are located away from each other circumferentially of the air cover to define air gaps, each between adjacent two of the crimped joints. The air inlet hole is formed in a portion of the protective cover closer to the top end thereof than the crimped joints, thereby minimizing the reach of foreign objects having entered at the air inlet hole to the ventilation filter to avoid the clogging of the ventilation filter.

The ventilation filter may be made of either of a porous PTFE or a sintered metal.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Referring to the drawings, wherein like reference numbers refer to like parts in several views, particularly to FIGS. 1 to 8, there is shown a gas sensor 1 according to the first embodiment of the invention which may be used in measuring the concentration of a given component of exhaust emissions of automotive engines. For instance, the gas sensor 1 may be designed as an $O_2$ sensor, an A/F sensor, or a NOx sensor.

The gas sensor 1 consists essentially of a sensor element 10 sensitive to a gas to be measured (which will also be referred to as a measurement gas below) to produce an electrical signal as a function of the concentration of the measurement gas, a housing 11 in which the sensor element 10 is retained, an air cover assembly 2 joined to a base end (i.e., an upper end, as viewed in FIG. 1) of the housing 11, leads 13 connecting electrically with the sensor element 10, and a cylindrical rubber bush 3 through which the leads 12 pass and which hermetically closes an end opening of the air cover assembly 2.

The rubber bush 3, as clearly illustrated in FIGS. 1 to 7, has vertical holes 314 and lead-pass holes 313 through which the leads 13 pass. Each of the vertical holes 314 serves as an air flow path and, as can be seen from FIG. 3, opens at a top end (i.e., a lower end, as viewed in the drawing) thereof to define an air outlet. The rubber bush 3 also has a first intermediate annular surface (i.e. a shoulder surface) 310 and a second intermediate annular surface (i.e., a shoulder surface) 320 which faces the first intermediate annular surface 310 and are away from each other through a neck 33.

An annular ventilation filter 4 is fitted on the neck 33 and nipped firmly between the first and second intermediate annular surfaces 310 and 320. Each of the vertical holes 314, as can be seen in FIG. 4, opens on the periphery of the neck 33 to define an air inlet and is covered with the ventilation filter 4, as illustrated in FIGS. 1 to 4 and 6. The ventilation filter 4, as can be seen from FIG. 1, projects slightly from the outer periphery of the rubber bush 3 to have a circumference exposed outside the rubber bush 3 fully.

Figure 1:
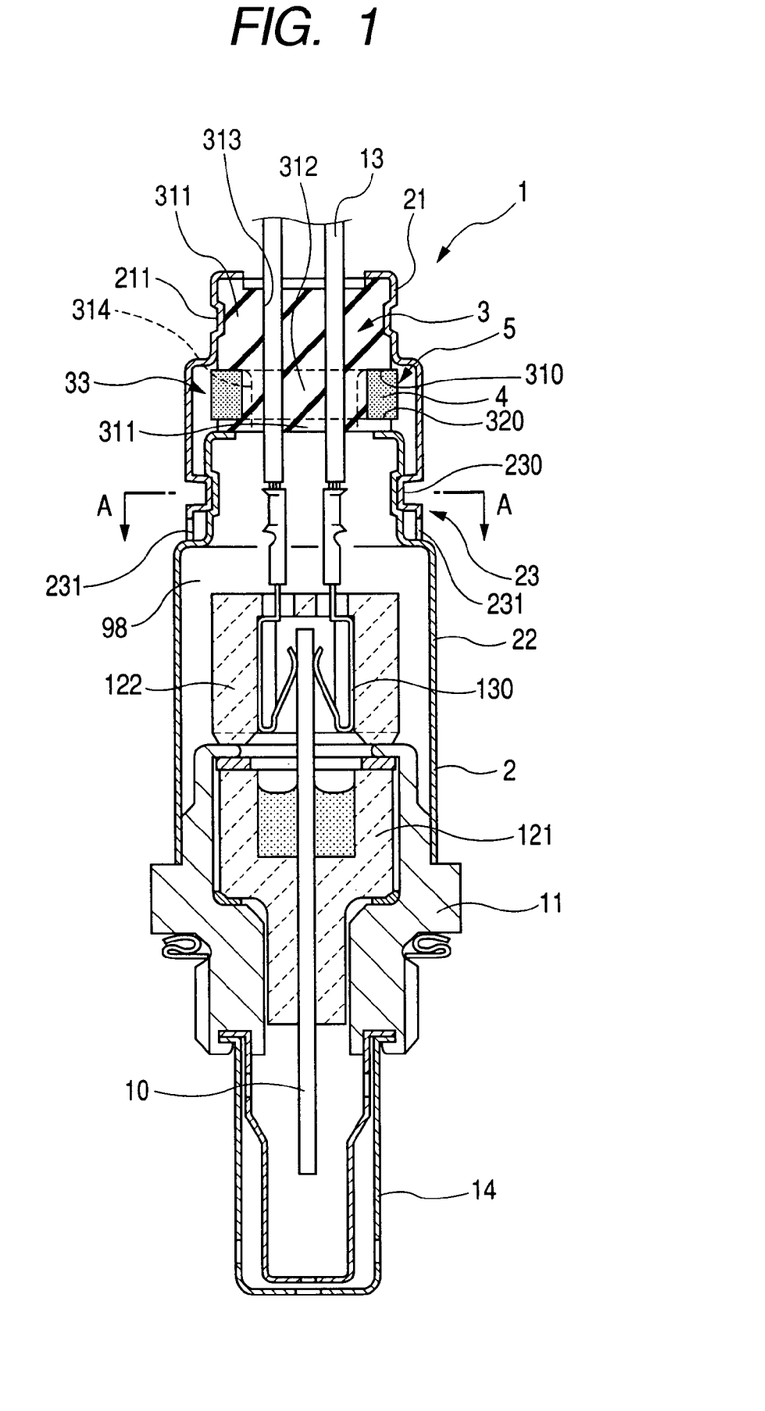
FIG. 1 is a longitudinal sectional view which shows an internal structure of a gas sensor according to the first embodiment of the invention.
Figure 2:
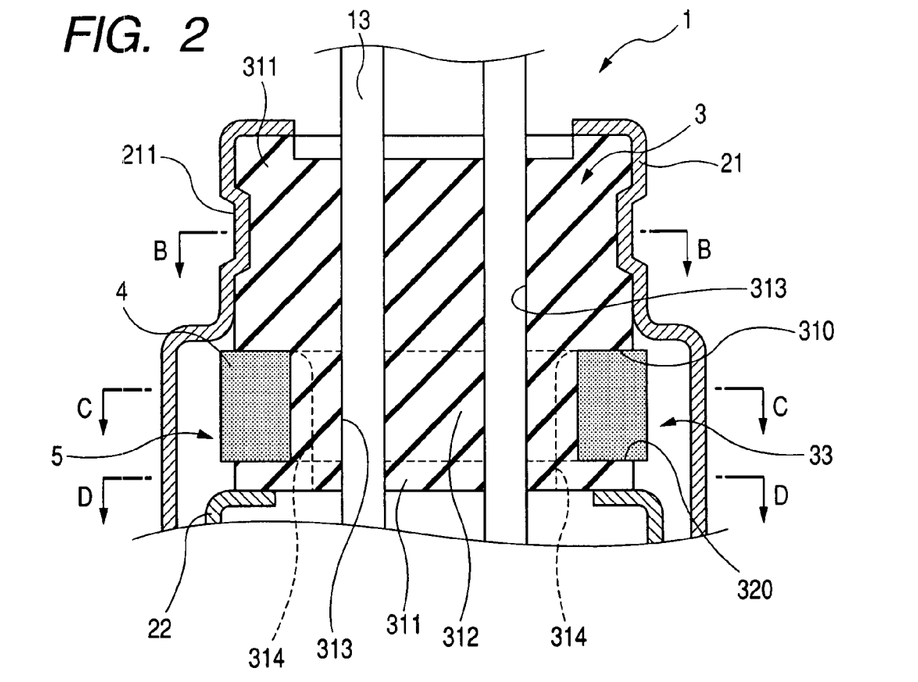
FIG. 2 is a partially enlarged longitudinal sectional view, as taken along the line E-E in FIG. 6, which shows a ventilation filer and a rubber bush installed in the gas sensor of FIG. 1.
Figure 3:
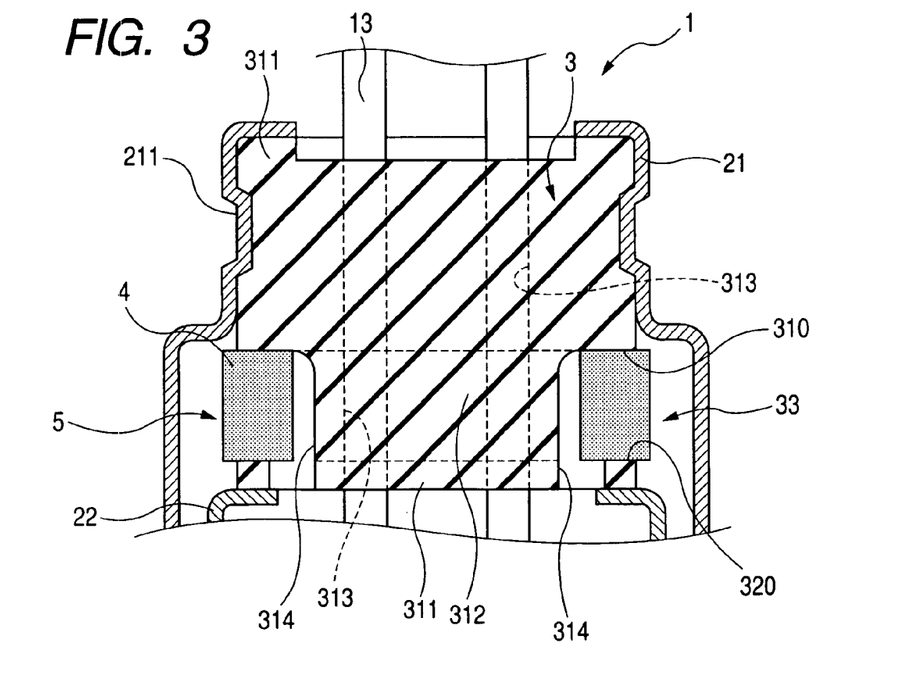
FIG. 3 is a partially enlarged longitudinal sectional view, as taken along the line F-F in FIG. 6, which shows a ventilation filer and a rubber bush installed in the gas sensor of FIG. 1.
Figure 4:
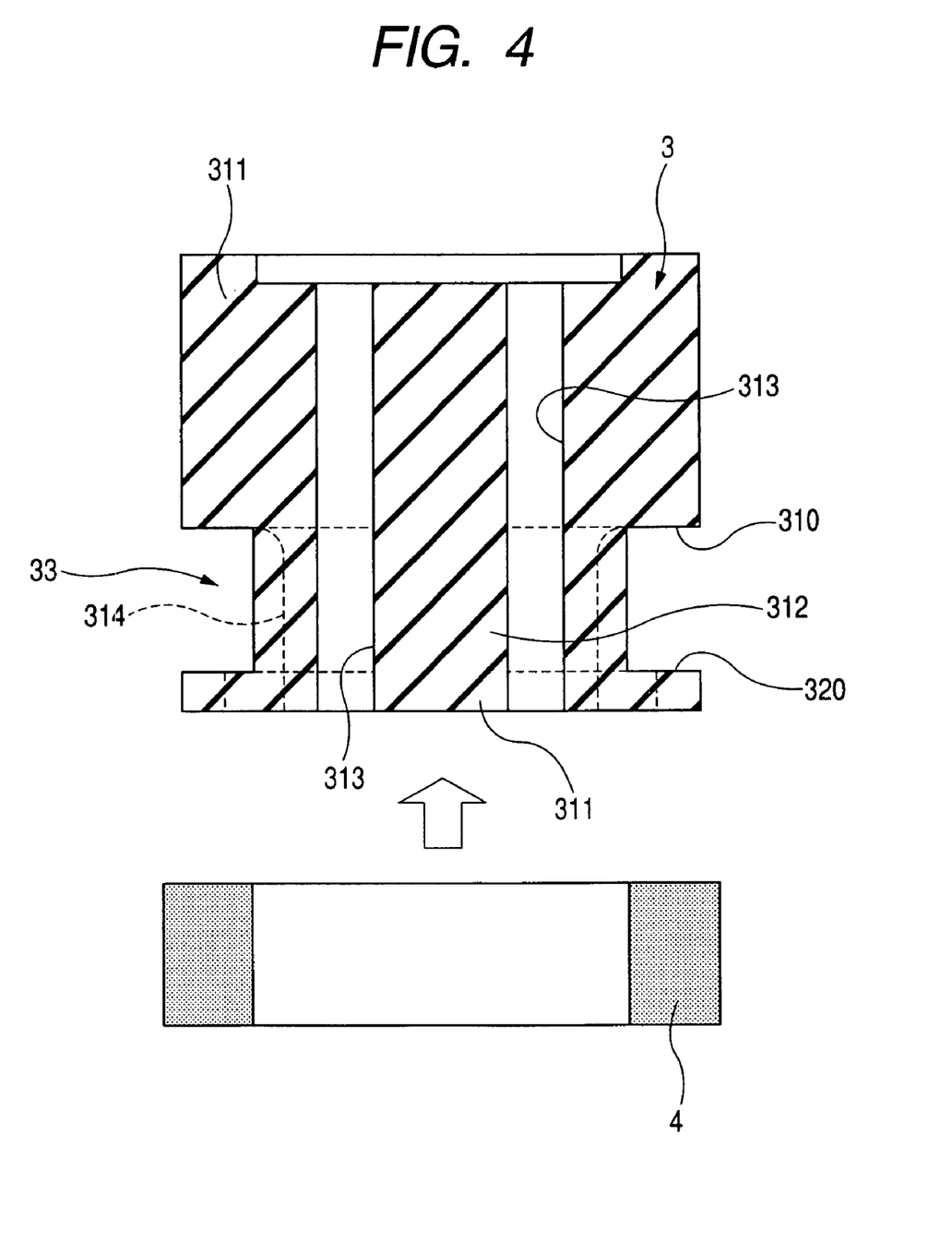
FIG. 4 is an exploded view which shows a rubber bush and a ventilation filter to be fitted on the rubber bush in the gas sensor of FIG. 1.
Figure 5:
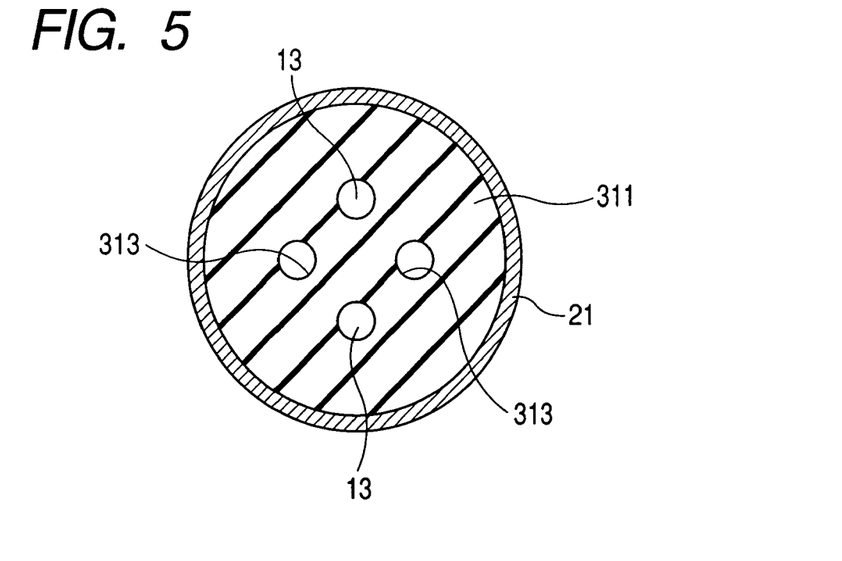
FIG. 5 is a transverse sectional view, as taken along the line B-B in FIG. 2.
Figure 6:
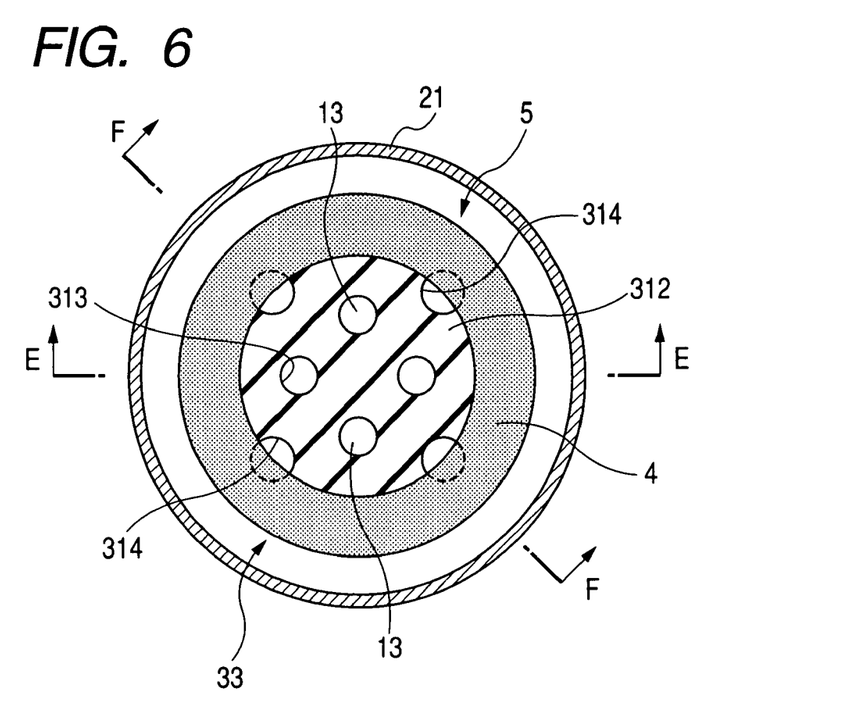
FIG. 6 is a transverse sectional view, as taken along the line C-C in FIG. 2.
Figure 7:
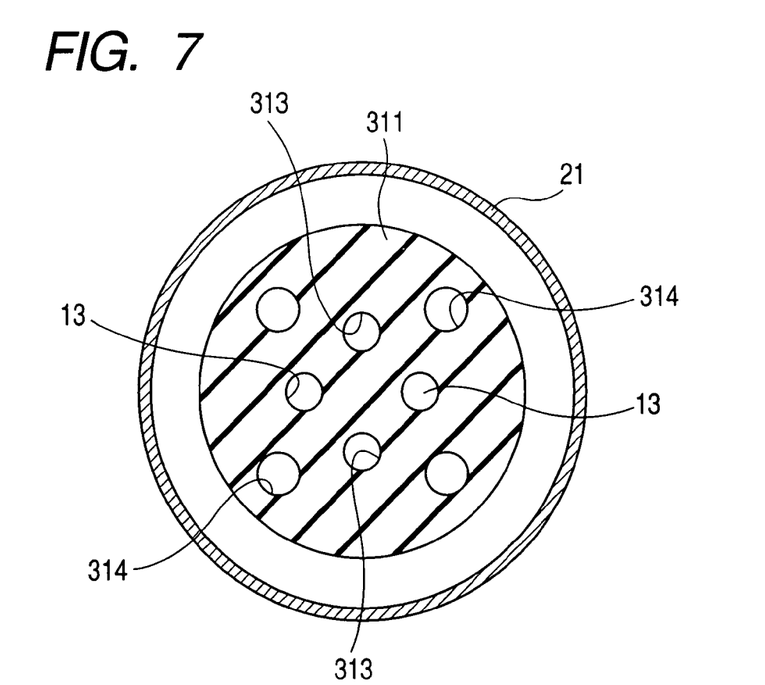
FIG. 7 is a transverse sectional view, as taken along the line D-D in FIG. 2.
Figure 8:
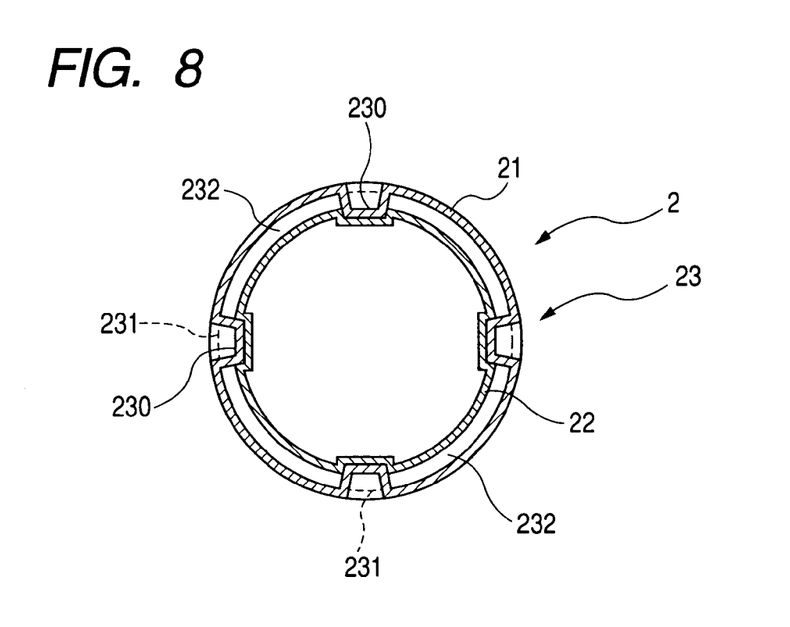
FIG. 8 is a transverse sectional view, as taken along the line A-A in FIG. 1.
Figure 9:
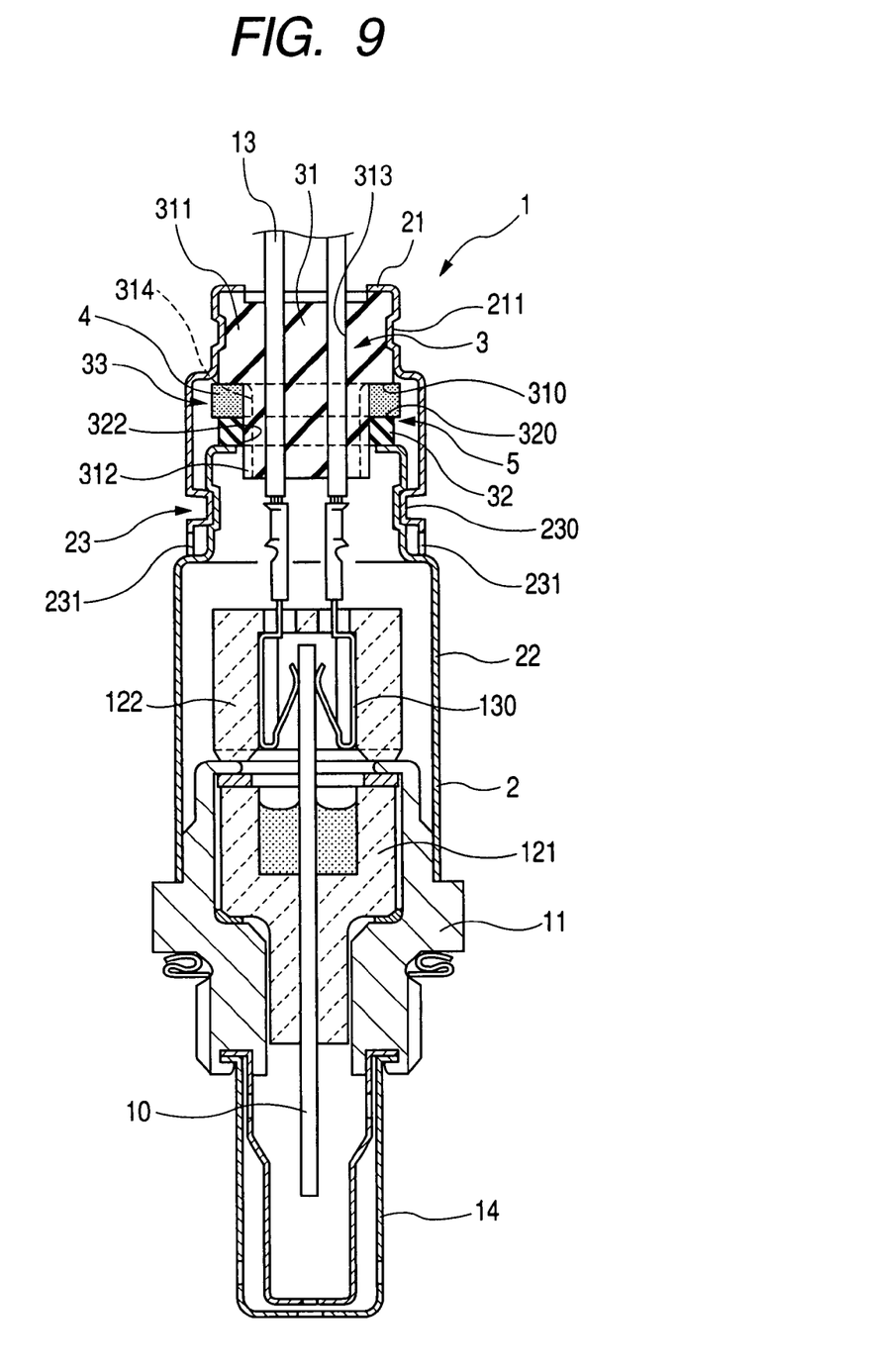
FIG. 9 is a longitudinal sectional view which shows an internal structure of a gas sensor according to the second embodiment of the invention.
Figure 10:
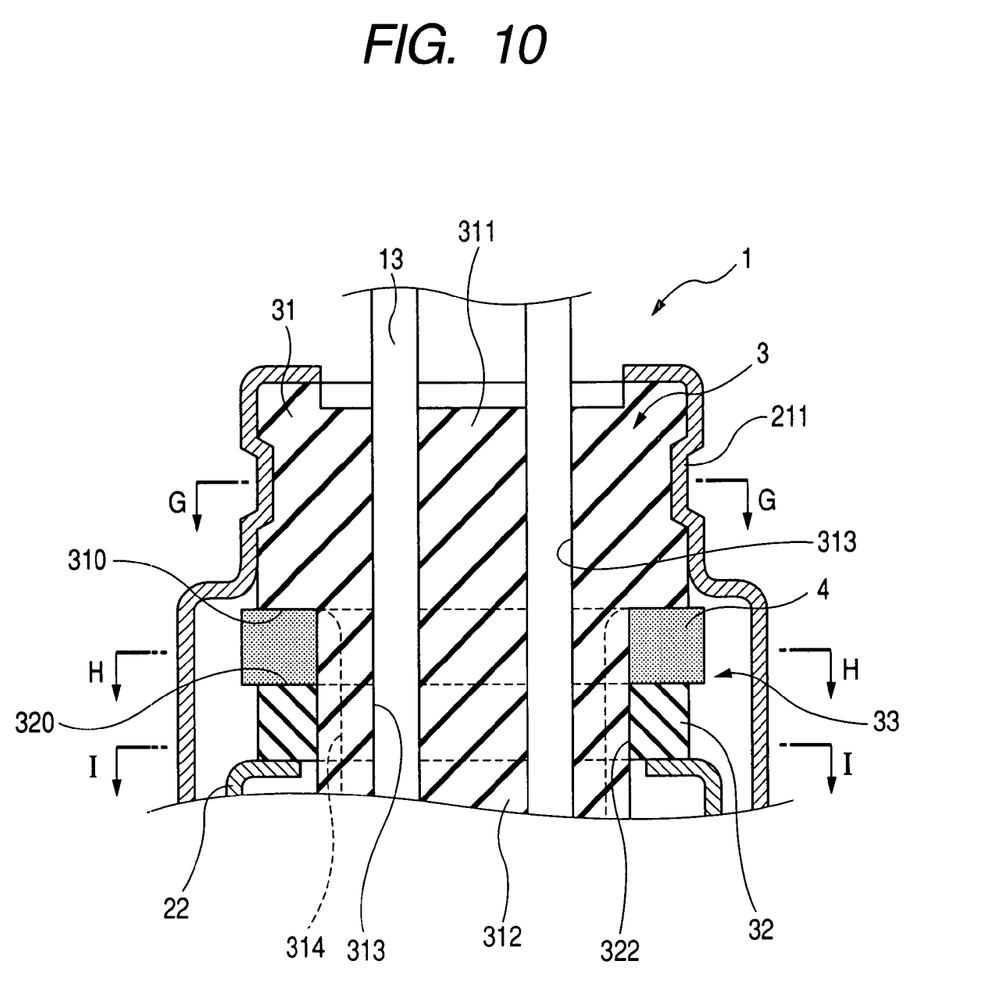
FIG. 10 is a partially enlarged longitudinal sectional view, as taken along the line J-J in FIG. 14, which shows a ventilation filer and a rubber bush installed in the gas sensor of FIG. 9.
Figure 11:
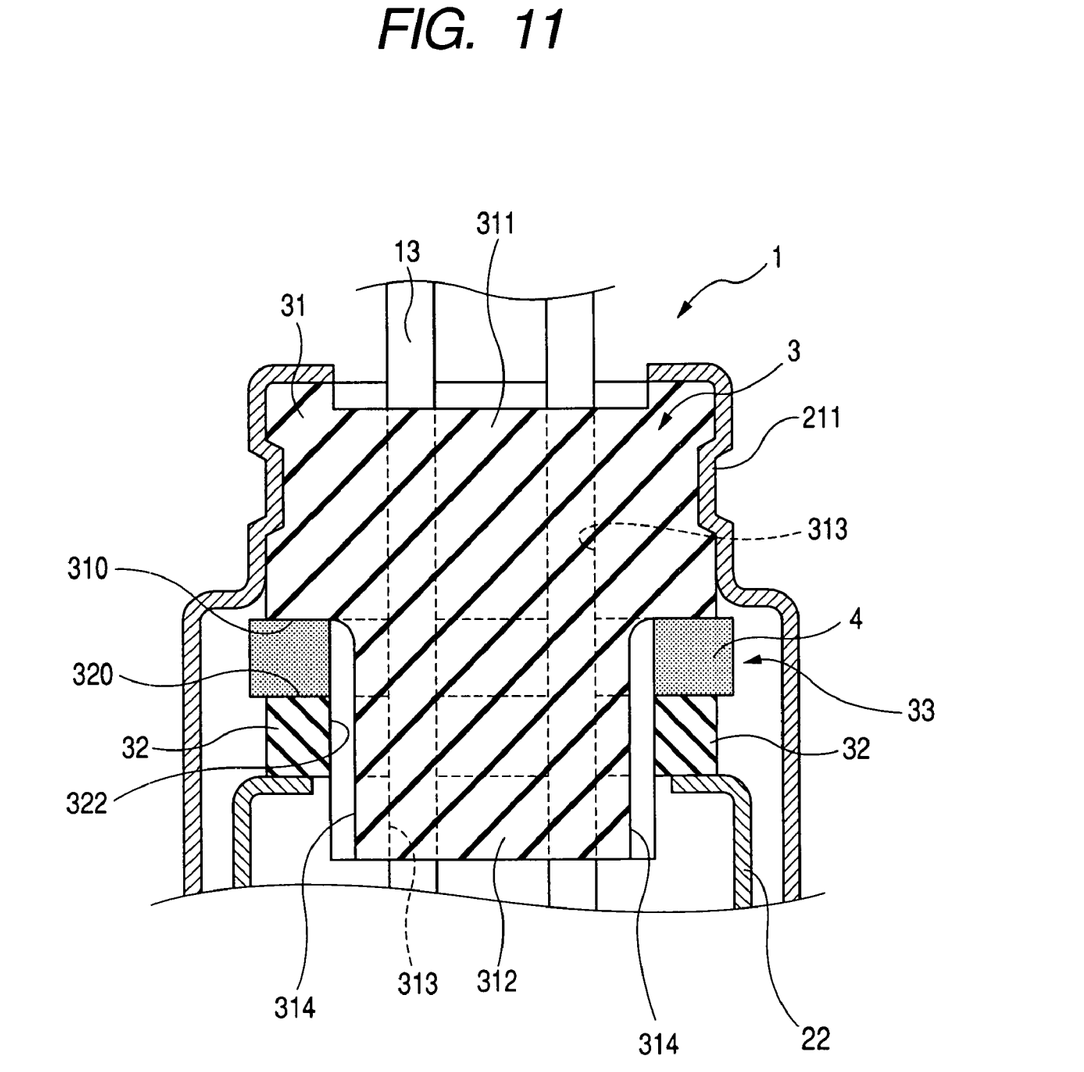
FIG. 11 is a partially enlarged longitudinal sectional view, as taken along the line K-K in FIG. 14, which shows a ventilation filer and a rubber bush installed in the gas sensor of FIG. 9.

The air cover 2 assembly is, as illustrated in FIGS. 1 to 3, squeezed or crimped radially inwardly to retain a portion of the rubber bush 3 closer to a base end (i.e., an upper end, as viewed in FIG. 1) thereof than the first intermediate annular surface 310 and also has an base end bent inwardly to form a vertical nip which holds the rubber bush 3 vertically. The air cover assembly 3 also has, as illustrated in FIGS. 1 and 8, air inlets 231 through which fresh air is admitted to the ventilation filter 4.

The structure of the gas sensor 1 will be described below in detail.

The sensor element 10 is, as can be seen from FIG. 1, retained inside a porcelain insulator 121 fitted within the housing 11. An air-exposed porcelain insulator 122 is mounted on the base end of the housing 11 to cover a base end portion of the sensor element 10. A protective cover assembly 14 is joined to the top end of the housing 11 to cover a top end portion of the sensor element 10.

The sensor element 10 is equipped with a gas-sensitive portion (i.e., the top end portion) working to output a signal as a function of the concentration of the measurement gas, a heater working to heat the gas-sensitive portion up to a desired activation temperature, and electric terminals (not shown) which connect electrically with the gas sensitive portion and the heater. The electric terminals are joined to the four leads 13 through connectors 130 disposed inside the air-exposed porcelain insulator 122.

The leads 13, as illustrated in FIGS. 1 to 3, extend inside the air cover assembly 2, pass through the lead-pass holes 313 of the rubber bush 3 fitted in the base end of the air cover assembly 2, and emerge outside the gas sensor 1.

The air cover assembly 2 is made up of a protective cover 21 and a support cover 22. The protective cover 21 is fit on a base end portion of the support cover 22 and surrounds the rubber bush 3. Specifically, the protective cover 21 has an annular neck 211 formed by crimping a circumferential portion thereof closer to the base end of the air cover assembly 2 than the first intermediate annular surface 310 of the rubber bush 3. The annular neck 211 will also be referred to as a crimped portion below. The crimped portion 211 exerts radial elastic pressure on the rubber bush 3 to retain it firmly within the protective cover 21 and also to establish a tight fit of each of the leads 13 within one of the lead-pass holes 313.

The protective cover 21 and the support cover 22 are joined firmly together through depressions or recesses 230 formed by inwardly crimping portions thereof which are, as clearly illustrated in FIG. 8, located at regular intervals in a circumferential direction of the air cover assembly 2 to define air gaps 232 between adjacent two of the recesses 230. Specifically, the protective cover 21 and the support cover 22 are joined together while undergoing elastic pressures which are produced by the recesses 230 and oriented radially and inwardly of the air cover assembly 3. The recesses 230 will also be referred to as crimped portions below.

The air inlets 231 are, as illustrated in FIG. 1, formed in the air cover assembly 21 closer to the top end of the air cover assembly 21 than joints 23 of the protective cover 21 and the support cover 22. The joints 23 are established by the crimped portions 230.

The rubber bush 3 is made of a one-piece rubber block which, as illustrated in FIGS. 1 to 7, has a small-diameter portion 312 and large-diameter portions 311. The small-diameter portions 312 is formed between the large-diameter portions 311 and defines the neck 33. The ventilation filter 4 is made of, for example, porous PTFE (polytetrafluoroethylene) and fit around the periphery of the small-diameter portion 312.

The rubber bush 3 is, as can be seen from FIGS. 1 to 3, compressed elastically between the base end of the protective cover 21 and the base end of the support cover 22.

The vertical holes 314 are formed in only a portion of the rubber bush 3 which is closer to the top end thereof than the first intermediate annular surface 310. Specifically, each of the vertical holes 314 extends only through the neck 33 (i.e., the small-diameter portion 312) and a lower one of the large-diameter portions 311 without occupying an upper one of the large-diameter portions 311 which is elastically compressed by the crimped portion 211 of the protective cover 21 of the air cover assembly 2.

The air gaps 5 are, as described above, formed between the protective cover 21 and the ventilation filter 4, thereby minimizing the amount of thermal energy transmitted from outside the gas sensor 1 to the ventilation filter 4 through the air cover assembly 2 to avoid the thermal deterioration of the ventilation filter 4.

An air path along which fresh air is introduced into the gas sensor 1 will be described below.

Fresh air entering at the air inlets 231 of the protective cover 21, as illustrated in FIGS. 1 to 3 and 8, passes through the air gaps 232 formed between the protective cover 21 and the support cover 22, and then reaches around the ventilation filter 4. The air, as illustrated in FIGS. 1 to 4 and 6, then passes through the ventilation filter 4 and enters the vertical holes (i.e., the air flow paths) 314. The ventilation filter 4 is, as described above, exposed at the overall circumference thereof to the air within the protective cover 21, thus facilitating ease of the entrance of the air into the vertical holes 314. The air flows out of the vertical holes 314 into an air chamber 98, as illustrated in FIG. 1, defined inside the support cover 22, enters the porcelain insulator 122, and is finally introduced into a reference gas chamber (not shown) defined inside the sensor element 10.

The beneficial advantages, as offered by the structure of the gas sensor 1, will be described below.

The annular ventilation filter 4 is press fit between the first intermediate annular surface 310 and the second intermediate annular surface 320 of the rubber bush 3, thereby ensuring the adhesion of the ventilation filter 4 to the rubber bush 3 even when the ventilation filter 4 is exposed to intense heat and shrunk. Specifically, when the ventilation filter 4 is thermally deteriorated and shrunk, the rubber bush 3 elastically expands to compensate for the amount of shrinkage of the ventilation filter 4, thereby keeping the fitting to the ventilation filter 4 to ensure a liquid-tight seal between the ventilation filter 4 and the rubber bush 3.

The air cover assembly 2, as illustrated in FIGS. 1 to 3 and 5, elastically grasps only a base end-side portion of the rubber bush 3 in which the lead-pass holes 313 are formed, thus ensuring a tight fit of each of the leads 13 within one of the lead-pass holes 313 without deforming the vertical holes 314 elastically. This maintains a liquid-tight seal between each of the leads 13 and one of the lead-pass holes 313 and also ensures the entrance of a desired amount of air into the gas sensor 1 through the vertical holes 314.

The ventilation filter 4 is, as illustrated in FIGS. 1 to 4 and 6, exposed at the overall circumference thereof to the air within the protective cover 21 and communicates with the air inlets of the vertical holes opening on the periphery of the neck 33 of the rubber bush 3, thus facilitating ease of the entrance of the air existing around the periphery of the ventilation filter 4 into the vertical holes 314.

The rubber bush 3 is designed to have the large-diameter portions 311 separated vertically from each other to define the neck 33 (i.e., the small-diameter portion 312) on which the ventilation filter 4 is press fit. The ventilation filter 4 is also press fit between the first and second intermediate annular surfaces 310 and 320. This assures the air/liquid tight seal between the ventilation filter 4 and the rubber bush 3.

The air cover assembly 2 is, as illustrated in FIGS. 1 to 3, made up of the protective cover 21 and the support cover 22. The protective cover 21 and the support cover 22 have the base ends (i.e., upper ends, as viewed in FIG. 1) which are bent inwardly to form a nip in which the rubber bush 3 is placed. This structure eliminates the need for complex machining of the air cover assembly 2 to retain the rubber bush 3.

The protective cover 21 and the support cover 21 are, as illustrated in FIGS. 1 and 8, connected together through the joints 23 (i.e., the crimped portions 230). The joints 23 define the air gaps 232 between the protective cover 21 and the support cover 22 and are located just above the air inlets 231, as viewed in FIG. 1. Specifically, each of the joints 23 lies between the ventilation filter 4 and one of the air inlets 231, thereby minimizing the reach of foreign objects having entered at the air inlets 231 to the ventilation filter 4 to avoid the clogging of the ventilation filter 4.

The ventilation filter 4 is made of a porous PTFE (polytetrafluoroethylene) and excellent in waterproofing property, thermal resistance, and mechanical durability.

The gas sensor 1 may alternatively be equipped with a known cup-shaped sensor element. The ventilation filter 4 may also be made of a porous sintered metal.

FIGS. 9 to 15 show the gas sensor 1 according to the second embodiment of the invention which is different from the first embodiment in that the rubber bush 3 is made of two parts: a cylindrical rubber block 31 and a rubber ring 32. Other arrangements are identical, and explanation thereof in detail will be omitted here.

Figure 12:
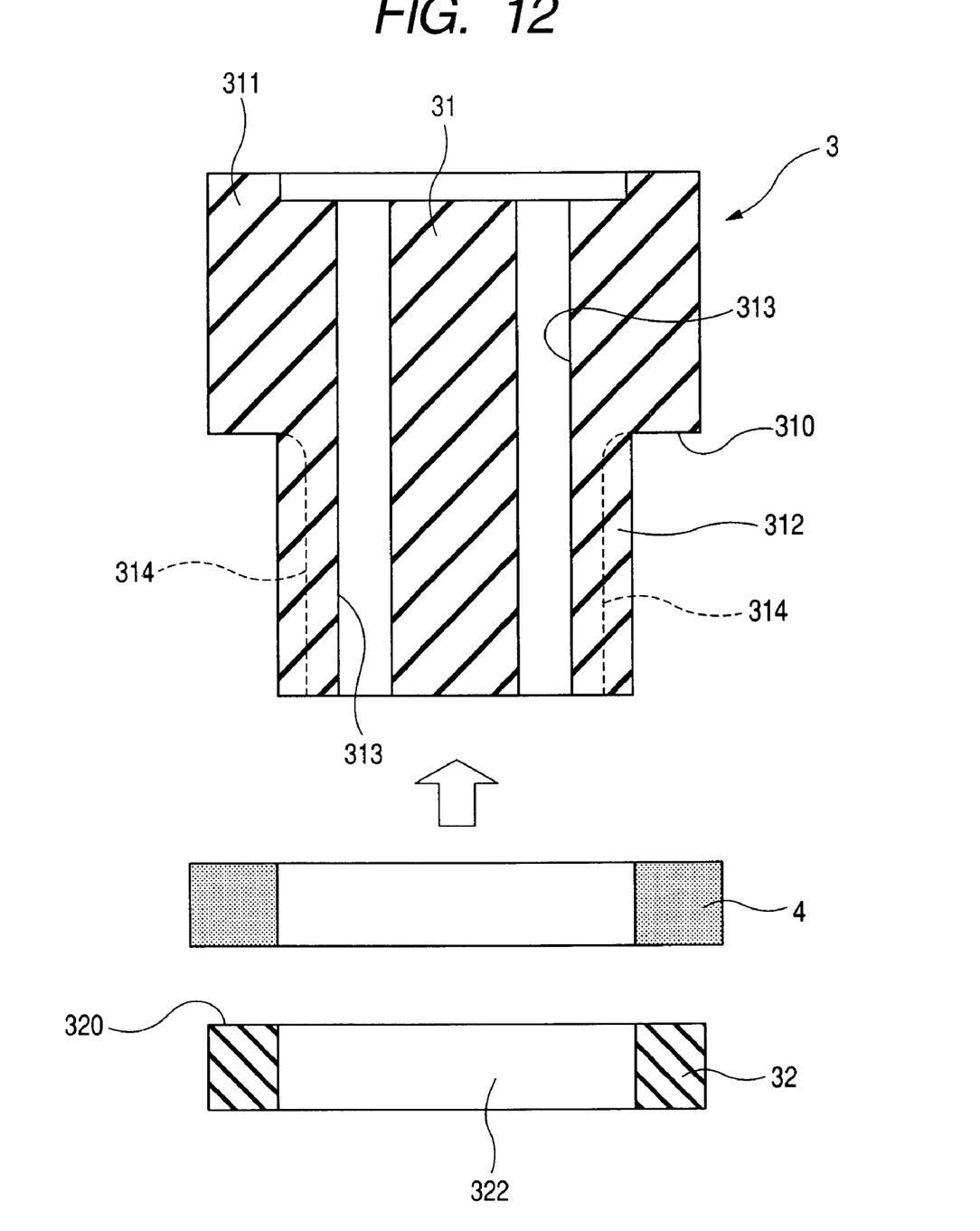
FIG. 12 is an exploded view which shows a rubber bush and a ventilation filter to be fitted on the rubber bush in the gas sensor of FIG. 9.
Figure 13:
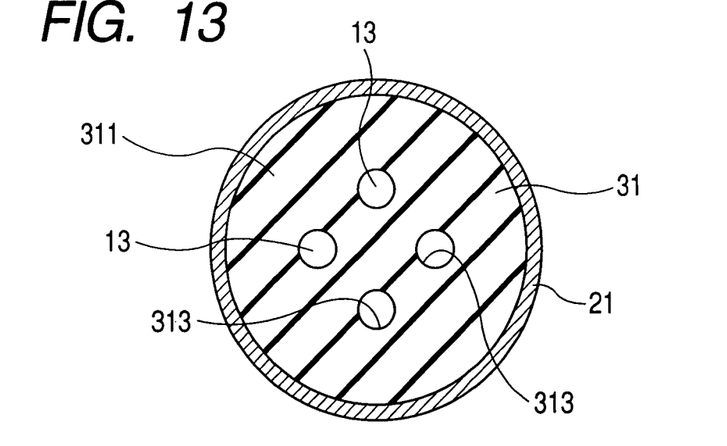
FIG. 13 is a transverse sectional view, as taken along the line G-G in FIG. 10.
Figure 14:
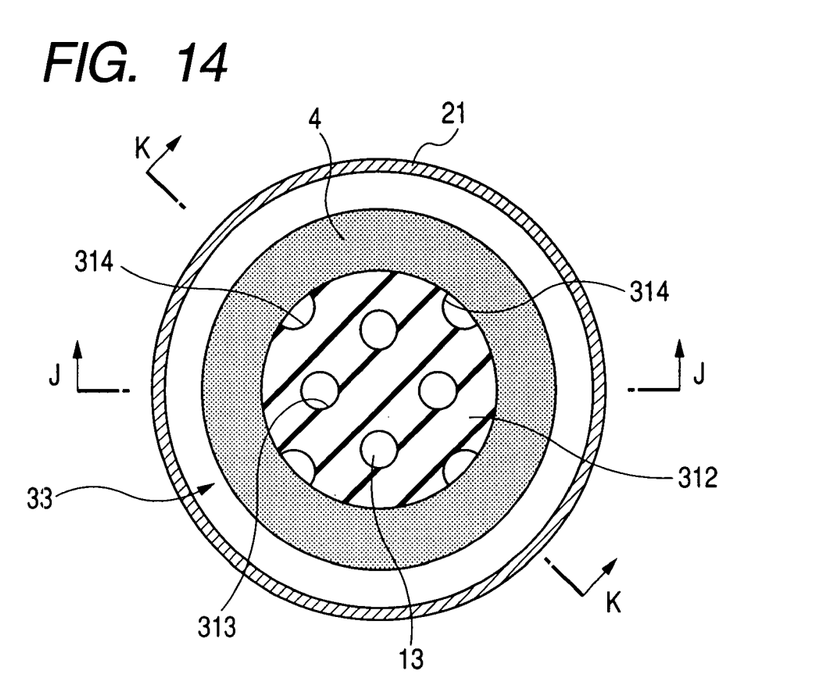
FIG. 14 is a transverse sectional view, as taken along the line H-H in FIG. 10.

The cylindrical rubber block 31 is, as clearly illustrated in FIG. 12, made up of the large-diameter portion 311 and the small-diameter portion 312 to define a shoulder surface as the first intermediate annular surface 310. The rubber ring 32 has a circular opening 322 fitted on the small-diameter portion 312 of the cylindrical rubber block 31 and also has an upper surface as the second intermediate annular surface 320.

Figure 15:
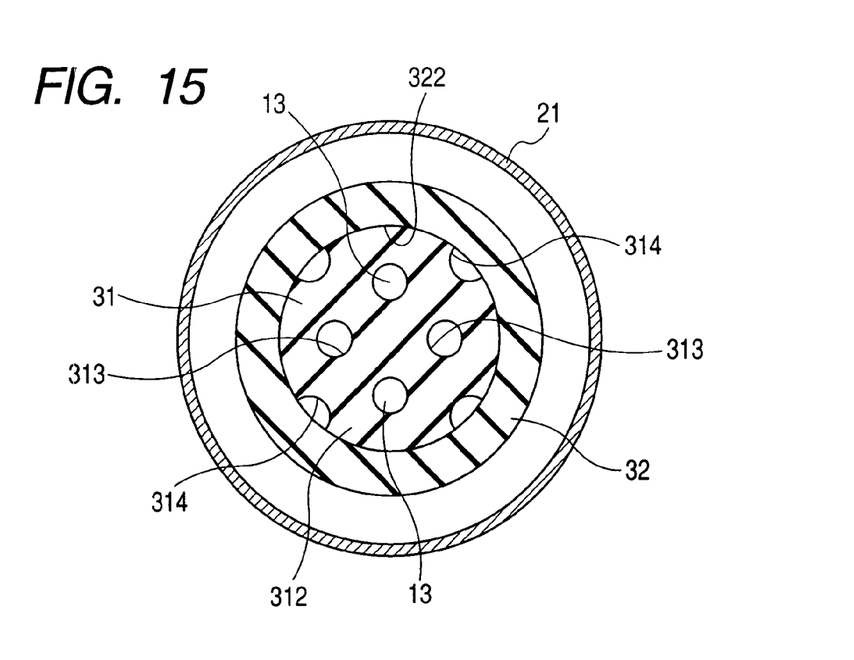
FIG. 15 is a transverse sectional view, as taken along the line I-I in FIG. 10.
Figure 16:
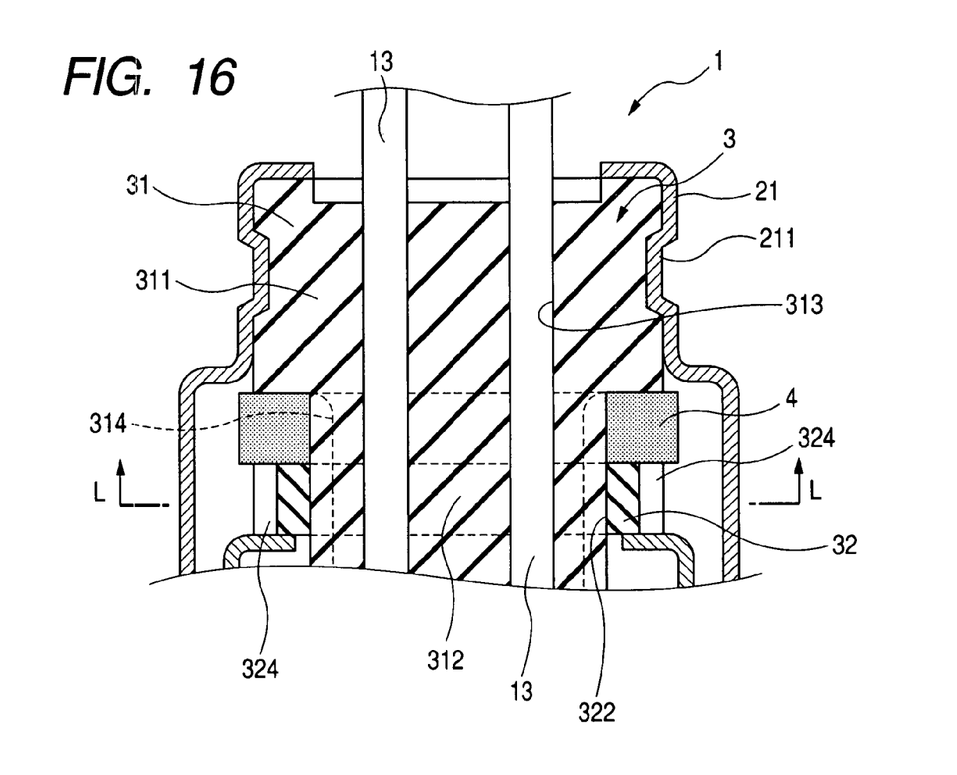
FIG. 16 is a partially enlarged longitudinal sectional view which shows an internal structure of a base end portion of a gas sensor according to the third embodiment of the invention.

U-shaped or half-pipe grooves are, as illustrated in FIGS. 12, 15, and 16, formed in the outer periphery of the small-diameter portion 312 of the cylindrical rubber block 31 as the vertical holes 314.

The ventilation filter 4 is nipped firmly between the first intermediate annular surface 310 of the cylindrical rubber block 31 and the second intermediate annular surface 320 of the rubber ring 32.

The rubber bush 3 is, as described above, made of two separate parts: the cylindrical rubber block 31 and the rubber ring 32, thus permitting the rubber bush 3 to be machined and assembled in a simpler manner than that in the first embodiment.

Figure 17:
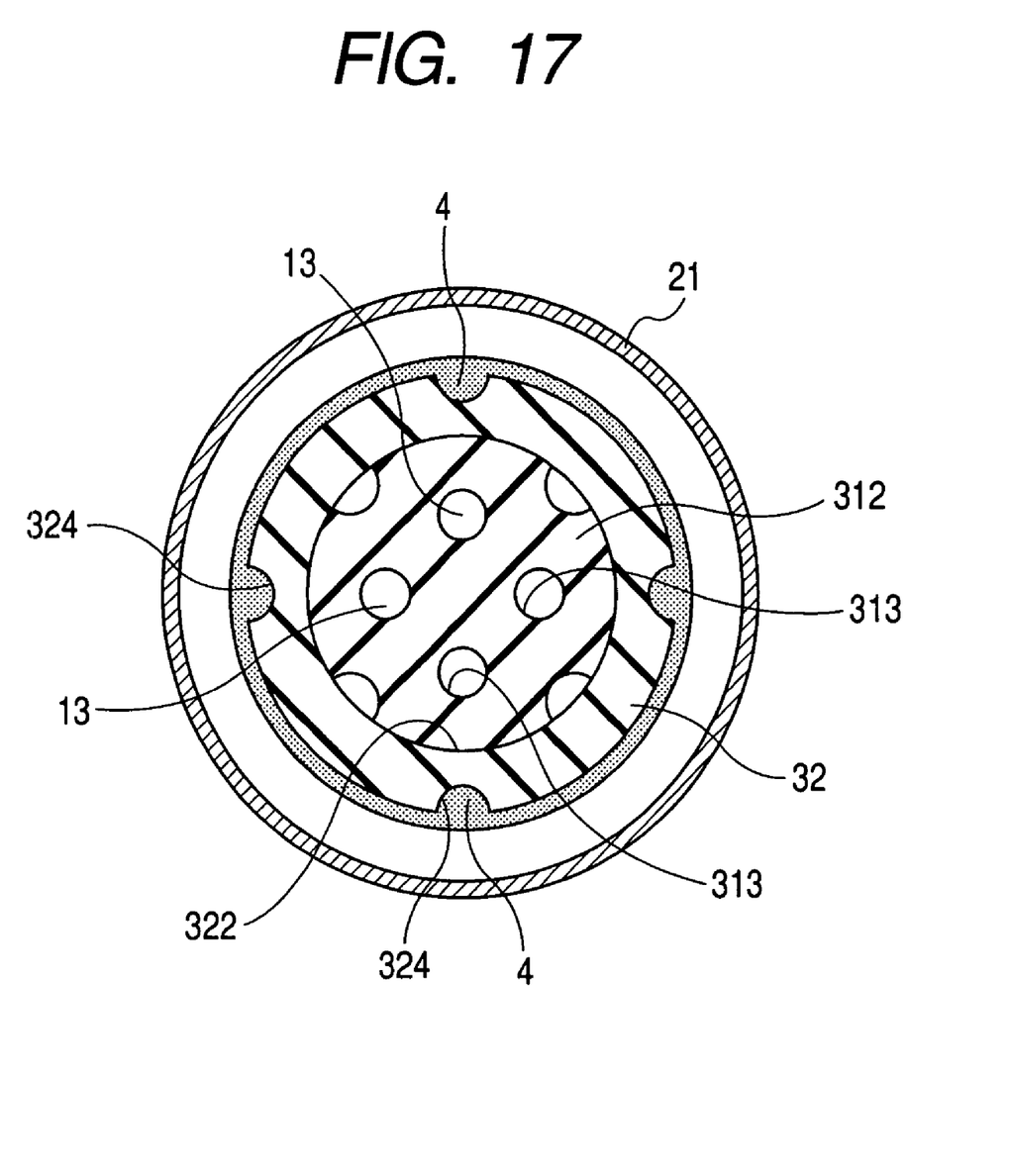
FIG. 17 is a transverse sectional view, as taken along the line L-L in FIG. 16.

FIGS. 16 and 17 show the gas sensor 1 according to the third embodiment of the invention which is a modification of the second embodiment.

The rubber ring 32 has formed in the outer periphery thereof four grooves 324 which extend in the thickness-wise direction of the rubber ring 32 (i.e., the axial direction of the gas sensor 1). Each of the grooves 324 is of a U-shape in transverse cross section.

The ventilation filter 4 has a lower surface partially exposed inside the grooves 324, as can be seen from FIG. 17, thus resulting in an increase in total area of the ventilation filter 4 exposed to the air, which facilitates ease of entrance of the air into the support cover 22.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas sensor having a length with a top end and a base end opposite the top end comprising:
   a sensor element sensitive to a gas to produce a signal as a function of concentration of the gas;
   a housing in which said sensor element is retained, said housing having a top end and a base end opposite the top end;
   an elastic block having holes through which leads pass to connect electrically with said sensor element, said elastic block being made up of a top portion closer to the top end of the gas sensor, a base portion closer to the base end of the gas sensor, and a neck formed between the top portion and the base portion, the base portion having a first shoulder surface, the top portion having a second shoulder surface facing the first shoulder surface in a lengthwise direction of the gas sensor;
   an air flow path extending within the top portion of said elastic block, said air flow path having an air inlet and an air outlet, the air inlet opening on an outer surface of the neck of said elastic block, the air outlet opening on a surface of the top portion of said elastic block exposed to an air chamber leading to said sensor element;
   an annular ventilation filter fitted on the neck of said elastic block in communication with the air inlet of said air flow path to permit air to enter said air flow path from outside said elastic block through said ventilation filter, said ventilation being nipped between the first and second shoulder surfaces of said elastic block;
   an air cover joined to said housing to extend away from the base end of the gas sensor to define therein the air chamber to which the air outlet of said air flow path is exposed, said air cover being crimped to provide a lateral elastic nip to the base portion of said elastic block in a direction perpendicular to the lengthwise direction of the gas sensor and also crimped to provide a longitudinal elastic nip to said elastic block in the lengthwise direction of the gas sensor; and
   an air inlet hole formed in said air cover through which the air is admitted to said ventilation filters,
   wherein the top portion and the base portion of said elastic block are made of discrete parts, the top portion and the base portion being arranged to provide a longitudinal elastic nip to said ventilation filter in the lengthwise direction of the gas sensor.

2. A gas sensor as set forth in claim 1, wherein the top portion and the base portion of said elastic block are greater in diameter than the neck, and wherein said ventilation filter is fitted around a periphery of the neck.

3. A gas sensor as set forth in claim 1, wherein the base portion has a small-diameter portion, and wherein the top portion is made of a ring member with an opening fit on the small-diameter portion of the base portion to define the neck of said elastic block.

4. A gas sensor as set forth in claim 1, wherein said ventilation filter is made of a porous polytetrafluoroethylene (PTFE).

5. A gas sensor having a length with a top end and a base end opposite the top end comprising:
   a sensor element sensitive to a gas to produce a signal as a function of concentration of the gas;
   a housing in which said sensor element is retained, said housing having a top end and a base end opposite the top end;
   an elastic block having holes through which leads pass to connect electrically with said sensor element, said elastic block being made up of a top portion closer to the top end of the gas sensor, a base portion closer to the base end of the gas sensor, and a neck formed between the top portion and the base portion, the base portion having a first shoulder surface, the tap portion having a second shoulder surface facing the first shoulder surface in a lengthwise direction of the gas sensor;
   an air flow path extending within the top portion of said elastic block, said air flow path having an air inlet and an air outlet, the air inlet opening on an outer surface of the neck of said elastic block, the air outlet opening on a surface of the top portion of said elastic block exposed to an air chamber leading to said sensor element;
   an annular ventilation filter fitted on the neck of said elastic block in communication with the air inlet of said air flow path to permit air to enter said air flow path from outside said elastic block through said ventilation filter, said ventilation being nipped between the first and second shoulder surfaces of said elastic block;
   an air cover joined to said housing to extend away from the base end of the gas sensor to define therein the air chamber to which the air outlet of said air flow path is exposed, said air cover being crimped to provide a lateral elastic nip to the base portion of said elastic block in a direction perpendicular to the lengthwise direction of the gas sensor and also crimped to provide a longitudinal elastic nip to said elastic block in the lengthwise direction of the gas sensor; and
   an air inlet hole formed in said air cover through which the air is admitted to said ventilation filter,
   wherein said air cover is made of an assembly of a protective cover and a support cover, the protective cover having a base end and a top end opposite the base end and surrounding said elastic block, the support cover having a base end and a top end opposite the base end, the protective cover being fitted on the support cover to elastically nip said elastic block between the base ends of the protective cover and the support cover in the lengthwise direction of the gas sensor.

6. A gas sensor as set forth in claim 5, wherein the protective cover is fitted on the support cover through crimped joints which are located away from each other circumferentially of said air cover to define air gaps, each between adjacent two of the crimped joints, and wherein the air inlet hole is formed in a portion of the protective cover closer to the top end thereof than the crimped joints.

7. A gas sensor having a length with a top end and a base end opposite the top end comprising:
   a sensor element sensitive to a gas to produce a signal as a function of concentration of the gas;
   a housing in which said sensor element is retained, said housing having a top end and a base end opposite the top end;
   an elastic block having holes through which leads pass to connect electrically with said sensor element, said elastic block being made up of a top portion closer to the top end of the gas sensor, a base portion closer to the base end of the gas sensor, and a neck formed between the top portion and the base portion, the base portion having a first shoulder surface, the top portion having a second shoulder surface facing the first shoulder surface in a lengthwise direction of the gas sensor;
   an air flow path extending within the top portion of said elastic block, said air flow path having an air inlet and an air outlet, the air inlet opening on an outer surface of the neck of said elastic block, the air outlet opening on a surface of the top portion of said elastic block exposed to an air chamber leading to said sensor element;
   an annular ventilation filter fitted on the neck of said elastic block in communication with the air inlet of said air flow path to permit air to enter said air flow path from outside said elastic block through said ventilation filter, said ventilation being nipped between the first and second shoulder surfaces of said elastic block;
   an air cover joined to said housing to extend away from the base end of the gas sensor to define therein the air chamber to which the air outlet of said air flow path is exposed, said air cover being crimped to provide a lateral elastic nip to the base portion of said elastic block in a direction perpendicular to the lengthwise direction of the gas sensor and also crimped to provide a longitudinal elastic nip to said elastic block in the lengthwise direction of the gas sensor; and
   an air inlet hole formed in said air cover through which the air is admitted to said ventilation filter,
   wherein said ventilation filter is made of a sintered metal.

* * * * *